(12) United States Patent
Wang et al.

(10) Patent No.: US 8,470,573 B2
(45) Date of Patent: Jun. 25, 2013

(54) HYBRID POLYMERASES HAVING THE ABILITY TO PRODUCE LONG AMPLICONS

(75) Inventors: Yan Wang, San Francisco, CA (US); John Sullivan, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 13 days.

(21) Appl. No.: 13/165,373

(22) Filed: Jun. 21, 2011

(65) Prior Publication Data

US 2012/0329126 A1   Dec. 27, 2012

(51) Int. Cl.
*C12N 9/12*   (2006.01)
*C12N 9/00*   (2006.01)
*C07K 1/00*   (2006.01)

(52) U.S. Cl.
USPC ............................ 435/194; 435/183; 530/350

(58) Field of Classification Search
USPC ................................. 530/350; 435/183, 194
See application file for complete search history.

(56) References Cited

U.S. PATENT DOCUMENTS

| 5,489,523 | A  | * | 2/1996 | Mathur ......................... 435/194 |
| 6,627,424 | B1 | * | 9/2003 | Wang ............................ 435/194 |
| 7,560,260 | B2 |   | 7/2009 | Vander Horn et al. |
| 2004/0002076 | A1 | | 1/2004 | Wang et al. |
| 2011/0104760 | A1 | | 5/2011 | Gong et al. |

FOREIGN PATENT DOCUMENTS

WO   WO 2004/011605 A2   2/2004

* cited by examiner

*Primary Examiner* — Maryam Monshipouri
(74) *Attorney, Agent, or Firm* — Kilpatrick Townsend & Stockton LLP

(57) ABSTRACT

The present invention provides DNA polymerases having increased efficiency of amplification of long amplicons. The present invention also provides for methods of amplifying target nucleic acid molecules with the DNA polymerases for increasing the efficiency of amplification of long amplicons.

8 Claims, 2 Drawing Sheets

Fig. 2

```
SEQ NO:2   1  MILDADYITEEGKPVIRLFKKENGKFKIEHDRTFRPYIYALLKDDSKIDEVRKITGERHG    60
              MILDADYITEEGKPVIRLFKKENG+FKIEHDRTFRPYIYALLKDDSKI+EV+KIT ERHG
SEQ NO:7   1  MILDADYITEEGKPVIRLFKKENGEFKIEHDRTFRPYIYALLKDDSKIEEVKKITAERHG    60

SEQ NO:2  61  KIVRIVDAEKVEKKFLGRPIEVWKLYLEHPQDVPAIRDKVREHPAVVDIFEYDIPFAKRY   120
              KIVRIVDAEKVEKKFLGRPI VW+LY EHPQDVP IR+K+REH AVVDIFEYDIPFAKRY
SEQ NO:7  61  KIVRIVDAEKVEKKFLGRPITVWRLYFEHPQDVPTIREKIREHSAVVDIFEYDIPFAKRY   120

SEQ NO:2 121  LIDKGLIPMEGEEELKILAFDIETLYHEGEEFGKGPIIMISYADENEAKVITWKNIDLPY   180
              LIDKGLIPMEG+EELK+LAFDIETLYHEGEEFGKGPIIMISYADE EAKVITWK IDLPY
SEQ NO:7 121  LIDKGLIPMEGDEELKLLAFDIETLYHEGEEFGKGPIIMISYADEEEAKVITWKKIDLPY   180

SEQ NO:2 181  VEVVSSEREMIKRFLRVIREKDPDVIITYNGDSFDFPYLVKRAEKLGIKLTIGRDGSEPK   240
              VEVVSSEREMIKRFL++IREKDPD+IITYNGDSFD PYL KRAEKLGIKLTIGRDGSEPK
SEQ NO:7 181  VEVVSSEREMIKRFLKIIREKDPDIIITYNGDSFDLPYLAKRAEKLGIKLTIGRDGSEPK   240

SEQ NO:2 241  MQRLGDMTAVEIKGRIHFDLYHVIRRTINLPTYTLEAVYEAIFGKPKEKVYADEIAEAWE   300
              MQR+GDMTAVE+KGRIHFDLYHVIRRTINLPTYTLEAVYEAIFGKPKEKVYADEIA+AWE
SEQ NO:7 241  MQRIGDMTAVEVKGRIHFDLYHVIRRTINLPTYTLEAVYEAIFGKPKEKVYADEIAKAWE   300

SEQ NO:2 301  SGEGLERVAKYSMEDAKVTYELGKEFLPMEIQLSRLVGQPLWDVSRSSTGNLVEWFLLRK   360
              +GEGLERVAKYSMEDAK TYELGKEF PME QLSRLVGQPLWDVSRSSTGNLVEWFLLRK
SEQ NO:7 301  TGEGLERVAKYSMEDAKATYELGKEFFPMEAQLSRLVGQPLWDVSRSSTGNLVEWFLLRK   360

SEQ NO:2 361  AYERNEVAPNKPSEEEYERRLRESYAGGYVKEPEKGLWENIVSLDFRSLYPSIIITHNVS   420
              AYERNE+APNKP E EYERRLRESYAGG+VKEPEKGLWENIVSLDFR+LYPSIIITHNVS
SEQ NO:7 361  AYERNELAPNKPDEREYERRLRESYAGGFVKEPEKGLWENIVSLDFRALYPSIIITHNVS   420

SEQ NO:2 421  PDTLNREGCREYDIAPEVGHKFCKDFPGFIPSLLKHLLEERQKIKTKMKESQDPIEKKML   480
              PDTLNREGCR YD+APEVGHKFCKDFPGFIPSLLK LL+ERQKIKTKMK SQDPIEK ML
SEQ NO:7 421  PDTLNREGCRNYDVAPEVGHKFCKDFPGFIPSLLKRLLDERQKIKTKMKASQDPIEKIML   480

SEQ NO:2 481  DYRQRAIKILANSFYGYYGYAKARWYCKECAESVTAWGRKYIEFVWKELEEKFGFKVLYI   540
              DYRQRAIKILANS+YGYYGYAKARWYCKECAESVTAWGR+YIEFVWKELEEKFGFKVLYI
SEQ NO:7 481  DYRQRAIKILANSYYGYYGYAKARWYCKECAESVTAWGREYIEFVWKELEEKFGFKVLYI   540

SEQ NO:2 541  DTDGLYATIPGGEPEEIKKKALEFVKYINSKLPGLLELEYEGFYVRGFFVTKKRYAVIDE   600
              DTDGLYATIPGG+ EEIKKKALEFV YIN+KLPGLLELEYEGFY RGFFVTKK+YA+IDE
SEQ NO:7 541  DTDGLYATIPGGKSEEIKKKALEFVDYINAKLPGLLELEYEGFYKRGFFVTKKKYALIDE   600

SEQ NO:2 601  EGKVITRGLEIVRRDWSEIAKETQARVLETILKHGNVEEAVKIVKEVTQKLANYEIPPEK   660
              EGK+ITRGLEIVRRDWSEIAKETQARVLE ILKHGNVEEAV+IVKEVTQKL+ YEIPPEK
SEQ NO:7 601  EGKIITRGLEIVRRDWSEIAKETQARVLEAILKHGNVEEAVRIVKEVTQKLSKYEIPPEK   660

SEQ NO:2 661  LAIYEQITRPLHEYKAIGPHVAVAKKLAARGVKIKPGMVIGYIVLRGDGPISKRAILAEE   720
              LAIYEQITRPLHEYKAIGPHVAVAK+LAA+GVKIKPGMVIGYIVLRGDGPIS RAILAEE
SEQ NO:7 661  LAIYEQITRPLHEYKAIGPHVAVAKRLAAKGVKIKPGMVIGYIVLRGDGPISNRAILAEE   720

SEQ NO:2 721  FDPRKHKYDAEYYIENQVLPAVLRILEGFGYRKEDLRWQKTKQVGLTSWLNIKKS        775
              +DPRKHKYDAEYYIENQVLPAVLRILEGFGYRKEDLRWQKTKQ GLTSWLNIKKS
SEQ NO:7 721  YDPRKHKYDAEYYIENQVLPAVLRILEGFGYRKEDLRWQKTKQTGLTSWLNIKKS        775
```

US 8,470,573 B2

HYBRID POLYMERASES HAVING THE ABILITY TO PRODUCE LONG AMPLICONS

BACKGROUND OF THE INVENTION

Nucleic acid amplification reactions, such as polymerase chain reaction (PCR), are generally template-dependent reactions in which a desired nucleic acid sequence is amplified by treating separate complementary strands of a target nucleic acid with an excess of two oligonucleotide primers. The primers are extended to form complementary primer extension products which act as templates for synthesizing the desired nucleic acid sequence. In such processes, the nucleic acid sequence between the primers on the respective DNA strands is selectively amplified. However, the efficiency of a nucleic acid amplification reaction, particularly for long amplicon sequences, can be negatively affected by a number of factors.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 2558-945.TXT, created on Oct. 28, 2011, 53,248 bytes, machine format IBM-PC, MS-Windows operating system, is hereby incorporated by reference in its entirety for all purposes.

BRIEF SUMMARY OF THE INVENTION

The present invention provides compositions and methods for amplifying a nucleic acid molecule. In one aspect, the present invention provides a polypeptide comprising a DNA polymerase having an amino acid sequence that is at least 95% (or at least 96%, 97%, 98%, or 99%) identical to SEQ ID NO:2.

In some embodiments, the DNA polymerase comprises SEQ ID NO:2.

In some embodiments, the polypeptide comprises a DNA polymerase having an amino acid sequence that is at least 95% (or at least 96%, 97%, 98%, or 99%) identical to SEQ ID NO:2, wherein the DNA polymerase is linked to a non-specific DNA binding domain. In some embodiments, the non-specific DNA binding domain comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:4. In some embodiments, the non-specific DNA binding domain comprises SEQ ID NO:4.

In some embodiments, the DNA polymerase linked to the non-specific DNA binding domain has a higher efficiency for amplification of an amplicon of at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:8. In some embodiments, the DNA polymerase linked to the non-specific DNA binding domain has a higher efficiency for amplification of an amplicon of at least 5 kb as compared to a DNA polymerase consisting of SEQ ID NO:8.

In some embodiments, the polypeptide comprises SEQ ID NO:5. In some embodiments, the polypeptide comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

In another aspect, the present invention provides for an isolated nucleic acid encoding a polypeptide of the present invention. In some embodiments, the isolated nucleic acid comprises a polynucleotide encoding a polypeptide comprising a DNA polymerase having an amino acid sequence at least 95% (or at least 96%, 97%, 98%, or 99%) identical to SEQ ID NO:2. In some embodiments, the isolated nucleic acid comprises a polynucleotide encoding a polypeptide comprising a DNA polymerase comprising SEQ ID NO:2. In some embodiments, the isolated nucleic acid comprises a polynucleotide encoding a polypeptide having a higher efficiency for amplification of an amplicon of at least 5 kb, at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:7.

In some embodiments, the isolated nucleic acid comprises a polynucleotide encoding a polypeptide comprising a DNA polymerase having an amino acid sequence at least 95% (or at least 96%, 97%, 98%, or 99%) identical to SEQ ID NO:2, wherein the DNA polymerase is linked to a non-specific DNA binding domain. In some embodiments, the non-specific DNA binding domain comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:4. In some embodiments, the non-specific DNA binding domain comprises SEQ ID NO:4. In some embodiments, the isolated nucleic acid comprises a polynucleotide encoding a DNA polymerase linked to the non-specific DNA binding domain that has a higher efficiency for amplification of an amplicon of at least 5 kb, at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:8.

In some embodiments, the isolated nucleic acid comprises a polynucleotide encoding a polypeptide comprising SEQ ID NO:5. In some embodiments, the isolated nucleic acid comprises a polynucleotide encoding a polypeptide comprising an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

In some embodiments, the isolated nucleic acid further comprises a promoter operably linked to the polynucleotide.

In another aspect, the present invention provides an isolated host cell comprising a heterologous expression cassette comprising a promoter operably linked to a polynucleotide encoding a polypeptide, the polypeptide comprising a DNA polymerase having an amino acid sequence at least 95% (or at least 96%, 97%, 98%, or 99%) identical to SEQ ID NO:2. In some embodiments, the DNA polymerase comprises SEQ ID NO:2. In some embodiments, the DNA polymerase, when linked to a non-specific DNA binding domain, has a higher efficiency for amplification of an amplicon of at least 5 kb, at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:7.

In some embodiments, the DNA polymerase is linked to a non-specific DNA binding domain. In some embodiments, the non-specific DNA binding domain comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:4. In some embodiments, the non-specific DNA binding domain comprises SEQ ID NO:4. In some embodiments, the DNA polymerase linked to the non-specific DNA binding domain has a higher efficiency for amplification of an amplicon of at least 5 kb, at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:8.

In some embodiments, the isolated host cell comprises a heterologous expression cassette comprising a promoter operably linked to a polynucleotide encoding a polypeptide, the polypeptide comprising SEQ ID NO:5 or comprising an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

In yet another aspect, the present invention provides methods of amplifying a nucleic acid molecule. In some embodiments, the method comprises incubating the target nucleic acid in a reaction mixture comprising at least one primer and a polypeptide comprising a DNA polymerase having an amino acid sequence at least 95% (or at least 96%, at least 97%, at least 98%, or at least 99%) identical to SEQ ID NO:2, wherein said incubating is under conditions that result in amplification of the target nucleic acid by the polypeptide; thereby amplifying the target nucleic acid.

In some embodiments, the polypeptide has a higher amplification efficiency amplification of an amplicon of at least 5 kb, at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:7.

In some embodiments, the DNA polymerase comprises SEQ ID NO:2.

In some embodiments, the DNA polymerase is linked to a non-specific DNA binding domain. In some embodiments, the non-specific DNA binding domain comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:4. In some embodiments, the non-specific DNA binding domain comprises SEQ ID NO:4. In some embodiments, the DNA polymerase linked to the non-specific DNA binding domain has a higher efficiency for amplification of an amplicon of at least 5 kb, at least 7 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:8.

In some embodiments, the polypeptide comprises SEQ ID NO:5. In some embodiments, the polypeptide comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

In still another aspect, the present invention provides reaction mixtures for amplifying a nucleic acid molecule. In some embodiments, the reaction mixture comprises a polypeptide comprising a DNA polymerase having an amino acid sequence at least 95% (or at least 96%, at least 97%, at least 98%, or at least 99%) identical to SEQ ID NO:2. In some embodiments, the DNA polymerase comprises SEQ ID NO:2.

In yet another aspect, the present invention provides kits for amplifying a nucleic acid molecule. In some embodiments, the kit comprises a polypeptide comprising a DNA polymerase having an amino acid sequence at least 95% (or at least 96%, at least 97%, at least 98%, or at least 99%) identical to SEQ ID NO:2. In some embodiments, the DNA polymerase comprises SEQ ID NO:2.

In some embodiments, the reaction mixture and/or kit comprises a polypeptide that has a higher amplification efficiency amplification of an amplicon of at least 5 kb, at least 7 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:7.

In some embodiments, the reaction mixture and/or kit comprises a polypeptide comprising a DNA polymerase having an amino acid sequence at least 95% (or at least 96%, 97%, 98%, or 99%) identical to SEQ ID NO:2, wherein the DNA polymerase is linked to a non-specific DNA binding domain. In some embodiments, the non-specific DNA binding domain comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:4. In some embodiments, the non-specific DNA binding domain comprises SEQ ID NO:4. In some embodiments, the DNA polymerase linked to the non-specific DNA binding domain has a higher efficiency for amplification of an amplicon of at least 5 kb, at least 7.5 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:8. In some embodiments, the polypeptide comprises SEQ ID NO:5. In some embodiments, the polypeptide comprises an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

DEFINITIONS

The term "polymerase" refers to an enzyme that performs template-directed synthesis of polynucleotides. The term encompasses both a full length polypeptide and a domain that has polymerase activity. DNA polymerases are well-known to those skilled in the art, including but not limited to DNA polymerases isolated or derived from *Pyrococcus furiosus*, *Thermococcus litoralis*, and *Thermotoga maritime*, or modified versions there of. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent. In some embodiments, a polymerase of the present invention is identical or substantially identical (e.g., has at least 60%, 65%, 70%, 75%, 80%, 85%, 90%, 91%, 92%, 93%, 94%, 95%, 96%, 97%, 98%, or 99% amino acid sequence identity) to SEQ ID NO:2 retaining at least one (and ins some embodiments, each) of the amino acids in SEQ ID NO:2 that are at the positions that vary between SEQ ID NO:2 and SEQ ID NO:7, while varying at other positions.

"Thermally stable polymerase," as used herein, refers to any enzyme that catalyzes polynucleotide synthesis by addition of nucleotide units to a nucleotide chain using DNA or RNA as a template and has an optimal activity at a temperature above 45° C.

The term "Sso7-like protein" or "Sso7," as used herein, refers to polypeptide variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity to SEQ ID NO:4 or 10; or that (2) bind to antibodies, e.g., polyclonal antibodies, raised against an immunogen comprising an amino acid sequence of SEQ ID NO:4 or 10. The term includes both full-length Sso7 polypeptides and fragments of the polypeptides that have sequence non-specific double-stranded binding activity. Sso7-like proteins include Sac7d, Sac7e, Ssh7b, and Sto7e.

A "domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity, or can have a stabilizing effect on the structure of the protein.

The term "DNA binding domain" refers to a protein domain that binds DNA in a sequence non-specific manner. In some embodiments, the DNA binding domain is a protein domain which binds with significant affinity to DNA, for which there is no known nucleic acid which binds to the protein domain with more than 100-fold more affinity than another nucleic acid with the same nucleotide composition but a different nucleotide sequence.

The term "polymerase-Sso7 conjugate," as used herein, refers to a modified polymerase comprising at least one Sso7 DNA binding domain joined to a polymerase domain, or a catalytic subunit of the polymerase domain. A polymerase-Sso7 conjugate may comprise multiple Sso7 DNA binding domains.

The terms "join" or "link" refer to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

The term "nucleic acid amplification" or "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

The term "amplification reaction mixture" or "amplification reaction composition" refers to an aqueous solution comprising the various reagents used to amplify a target nucleic acid. These include enzymes, aqueous buffers, salts, amplification primers, target nucleic acid, and nucleoside triphosphates. As discussed further herein, amplification reaction mixtures may also further include stabilizers and other additives to optimize efficiency and specificity. Depending upon the context, the mixture can be either a complete or incomplete amplification reaction mixture.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

The term "increased efficiency" or "improved efficiency," as used with respect to nucleic acid amplification, refers to a detectable increase in the amount of amplification products produced in a nucleic acid amplification during a specified number of rounds (i.e., cycles) of amplification in the presence of a DNA polymerase of the present invention as compared to the amount of amplification products produced in a nucleic acid amplification during a specified number of rounds (i.e., cycles) of amplification in the presence of a control DNA polymerase. Efficiency of an amplification reaction can be measured according to any method, including but not limited to melt-curve analysis or gel analysis. In some embodiments, an amplification reaction in the presence of a DNA polymerase of the present invention will exhibit at least 10%, 15%, 20%, 25%, 30%, 40%, 50%, 100%, 2-fold (200%), 2.5-fold (250%), 3-fold (300%) or greater increase in the amount of amplification products produced in a given number of cycles as compared to the amount of amplification products produced in the same number of cycles using a control DNA polymerase (e.g., a DNA polymerase consisting of SEQ ID NO:7 or SEQ ID NO:8).

An "olignucleotide primer" or "primer" refers to an oligonucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides in length. The length and sequences of primers for use in PCR can be designed based on principles known to those of skill in the art; see, e.g., Innis et al., supra.

The term "amplicon" refers to a polynucleotide (e.g., DNA) fragment formed as the product of a natural or artificial amplification event (e.g., polymerase chain reaction). In some embodiments, an amplicon is a "long" amplicon having a length of at least 5 kb, or at least 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 31 kb, 22 kb, 23 kb, 24 kb, 25 kb, 26 kb, 27 kb, 28 kb, 29 kb, 30 kb, 31 kb, 32 kb, 33 kb, 34 kb, 35 kb, 36 kb, 37 kb, 38 kb, 39 kb, or 40 kb.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-0-methyl ribonucleotides, and peptide nucleic acids (PNAs).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "promoter" refers to regions or sequences located upstream and/or downstream from the start of transcription and which are involved in recognition and binding of RNA polymerase and other proteins to initiate transcription.

The terms "identical" or percent "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity) over a specified region where indicated, or across the entire reference sequence if not otherwise indicated, when compared and aligned for maximum correspondence over a comparison window, or designated region as measured using one of the following sequence comparison algorithms or by manual alignment and visual inspection. These definitions also refer to the complement of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of contiguous positions, for example from 20 to 600 contiguous positions, about 50 to about 200, or about 100 to about 150, in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

BRIEF DESCRIPTION OF THE DRAWINGS

FIG. 2. Sequence alignment comparing the amino acid sequence of the DNA polymerase of SEQ ID NO:2 with the amino acid sequence of the DNA polymerase of SEQ ID NO:7. Consensus=SEQ ID NO:17.

DETAILED DESCRIPTION

I. Introduction

Figure 1:
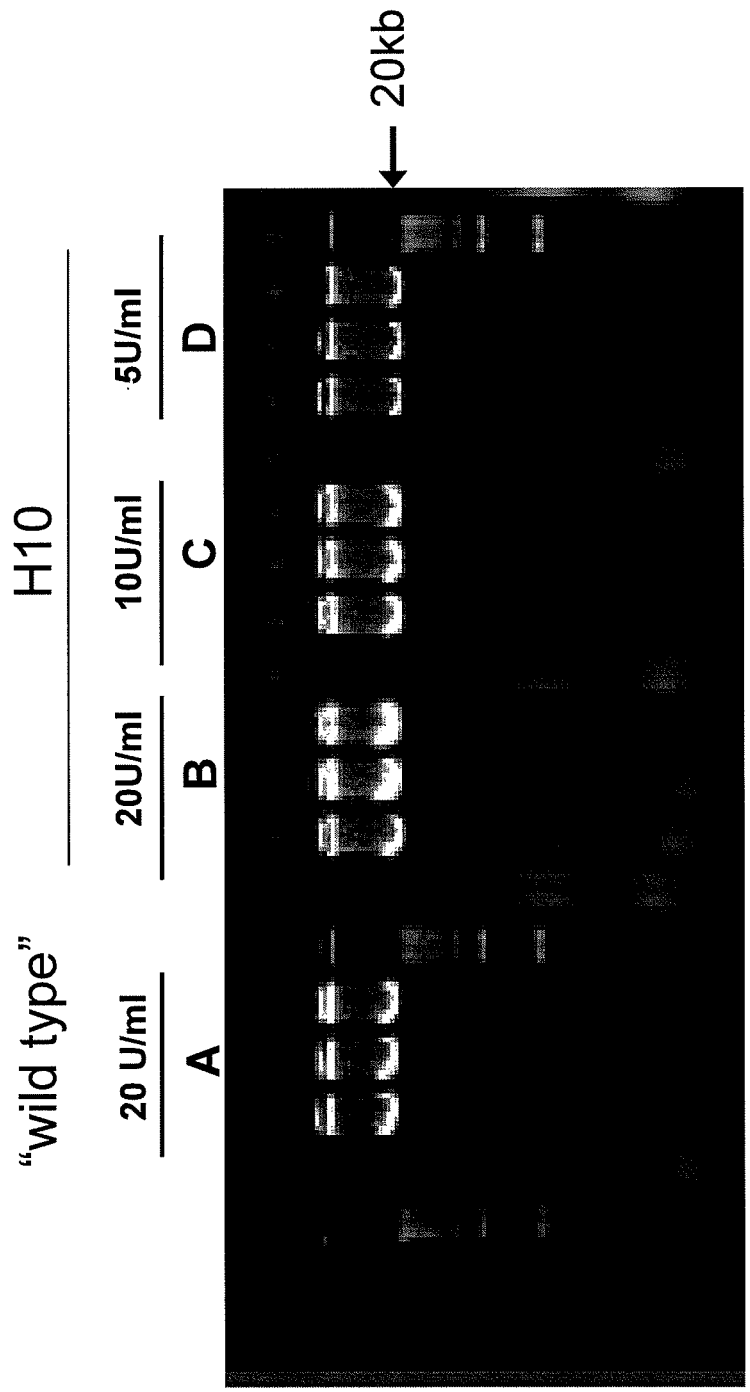
FIG. 1. H10 fusion polymerase has a higher efficiency than wild-type fusion polymerase in amplifying a 20 kb target from lambda DNA. The increase in efficiency is reflected by the higher yield of the final product when equal units of enzyme were used (compare A and B), or the need for less enzyme to produce the same yield (compare A and C).

The present invention provides methods and compositions for improving the efficiency of nucleic acid amplification, in particular in improving the efficiency of long amplicons. A DNA polymerase having improved activities has been discovered. The DNA polymerase was initially identified as a polymerase having a polymerase activity greater than its 3'-5' exonuclease activity. It was further discovered that the DNA polymerases has substantially better ability (as determined by amplicon yield) to amplify long (e.g., 7.5 or 20 kb) amplicons as compared to SEQ ID NOs:7 or 8.

Thus, in one aspect, the present invention provides a polypeptide comprising a DNA polymerase having an amino acid sequence that is at least 95% identical to SEQ ID NO:2. In some embodiments, the polypeptide has higher efficiency for amplification of a long amplicon (e.g., an amplicon of at least 5 kb, at least 7.5 kb, at least 10 kb, at least 15 kb, or at least 20 kb) as compared to a DNA polymerase consisting of SEQ ID NO:7. In some embodiments, the polypeptide comprises a DNA polymerase having an amino acid sequence at least 95% identical to SEQ ID NO:2 linked to a non-specific DNA binding domain, e.g., a non-specific DNA binding domain comprising an amino acid sequence that is at least 80%, 85%, 90%, 95%, 99%, or 100% identical to SEQ ID NO:4.

In another aspect, the present invention provides methods of amplifying a nucleic acid molecule. In some embodiments, the method comprises incubating the target nucleic acid in a reaction mixture comprising at least one primer and a polypeptide comprising a DNA polymerase having an amino acid sequence that is at least 95% identical to SEQ ID NO:2, wherein said incubating is under conditions that result in amplification of the target nucleic acid by the polymerase, thereby amplifying the target nucleic acid. In some embodiments, the polymerase comprises a DNA polymerase having an amino acid sequence at least 95% identical to SEQ ID NO:2 linked to a non-specific DNA binding domain, e.g., a non-specific DNA binding domain comprising an amino acid sequence that is at least 80%, 85%, 90%, 95%, 99%, or 100% identical to SEQ ID NO:4.

In still another aspect, the present invention provides reaction mixtures and/or kits for performing nucleic acid amplification reactions that use polymerases. In some embodiments, the reaction mixtures and/or kits comprise a polypeptide comprising a DNA polymerase having an amino acid sequence that is at least 95% identical to SEQ ID NO:2. In some embodiments, the reaction mixtures and/or kits comprise a polypeptide comprising a DNA polymerase having an amino acid sequence at least 95% identical to SEQ ID NO:2 and linked to a non-specific DNA binding domain, e.g., a non-specific DNA binding domain comprising an amino acid sequence that is at least 80%, 85%, 90%, 95%, 99%, or 100% identical to SEQ ID NO:4.

II. Polymerases of the Invention

An exemplary polymerase of the invention comprises SEQ ID NO:2 or at least comprises a polypeptide substantially identical across the full-length of SEQ ID NO:2. These polymerases are synthetic, non-naturally-occurring polymerases.

Variants of SEQ ID NO:2 that substantially retain the polymerase activity of SEQ ID NO:2 can be generated, for example, by retaining each of the amino acids in SEQ ID NO:2 that are at the positions that vary between SEQ ID NO2 and SEQ ID NO:7, while varying other positions. One of skill in the art can determine the positions that vary between SEQ ID NO:2 and SEQ ID NO:7, and thus determine positions which positions to retain and/or which positions to vary from SEQ ID NO:2, by reference to a sequence alignment, for example a sequence alignment shown in FIG. 2. It will be further appreciated that some positions in the polymerase as highly conserved across different polymerases and thus variation in such positions are more likely to alter or harm polymerase activity than positions that are variable between polymerases. An example of a sequence conserved between SEQ ID NO:2 and other polymerases is YGYYGYAKARWYCK-ECAESVTAWGR (SEQ ID NO:9). See, e.g., U.S. Pat. No. 7,560,260. Thus in some embodiments, the polymerases of the invention are substantially identical to SEQ ID NO:2 and comprise SEQ ID NO:9 as well as retaining each of the amino acids in SEQ ID NO:2 that are at the positions that vary between SEQ ID NO2 and SEQ ID NO:7. In some embodiments, the polymerases of the invention comprise a polypeptide at least 95% identical to SEQ ID NO:2.

In one aspect, the polymerases of the invention are characterized by having a high efficiency at amplifying long amplicons (e.g., an amplicon of at least 5 kb, at least 7.5 kb, at least 10 kb, at least 15 kb, or at least 20 kb). For example, in some embodiments, the polymerases of the invention are more efficient (i.e., yield more product) in a nucleic acid amplification reaction than a polymerase comprising SEQ ID NO:7. In some embodiments, the polymerases of the invention are more efficient (i.e., yield more product) in a nucleic acid amplification reaction than a polymerase comprising SEQ ID NO:8.

In some embodiments, polymerases of the invention comprise mutations that render the polymerase exonuclease deficient. "Exonuclease deficient" as used herein means that the polymerase has a substantially reduced (i.e., less than 10%, 5% or 1% of the 3'-5' exonuclease activity of Pfu DNA polymerase from *Pyrococcus furiosus*) or no exonuclease activity. For example, a double point mutation in the polymerase domain substituting an alanine at positions D141 and E143 can remove or eliminate 3'-5' exonuclease activity. See, e.g., Derbyshire et al., *Methods in Enzymology*, Vol 262 (1995), pages 363-385. Hybrid polymerases comprising such double point mutations will generally show an increased specificity in nucleic acid amplification reactions, resulting in fewer amplification byproducts (such as amplification of primer-dimers) and increased efficiency in amplification of the desired target nucleic acids.

In some embodiments, the polymerases (including hybrid polymerases) of the invention can be in isolated form. In some embodiments, the polymerases (including hybrid polymerases) are lyophilized. Alternatively, the polymerases (including hybrid polymerases) are in soluble form in an aqueous solution. In some embodiments, the polymerases (including hybrid polymerases) are produced recombinantly and thus are within an intact cell or in a cell lysate.

Nucleic Acid Binding Domains

In some embodiments, the polymerases of the invention are fused to a DNA binding domain. Such fusions are sometimes referred to herein as "hybrid polymerases." A DNA binding domain is a protein, or a defined region of a protein, that binds to nucleic acid in a sequence-independent matter, e.g., binding does not exhibit a gross preference for a particular sequence. DNA binding domains may bind single or double stranded nucleic acids.

The DNA binding proteins of use in the invention are generally thermostable. Examples of such proteins include, but are not limited to, the Archaeal small basic DNA binding proteins Sso7d and Sso7d-like proteins (see, e.g., Choli et al., Biochimica et Biophysica Acta 950:193-203, 1988; Baumann et al., Structural Biol. 1:808-819, 1994; and Gao et al, Nature Struc. Biol. 5:782-786, 1998), Archaeal HMf-like proteins (see, e.g., Starich et al., J. Molec. Biol. 255:187-203, 1996; Sandman et al., Gene 150:207-208, 1994), and PCNA homologs (see, e.g., Cann et al., J. Bacteriology 181:6591-6599, 1999; Shamoo and Steitz, Cell:99, 155-166, 1999; De Felice et al., J. Mol. Biol. 291, 47-57, 1999; and Zhang et al., Biochemistry 34:10703-10712, 1995).

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

Certain helix-hairpin-helix motifs have been shown to bind DNA nonspecifically and enhance the processivity of a DNA polymerase to which it is fused (Pavlov et al., Proc Natl Acad Sci USA. 99:13510-5, 2002).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_m$ of DNA by up to 40° C. under some conditions (McAfee, Biochemistry 34:10063-10077, 1995; Gao et al., Nat. Struct. Biol. 5(9):782-786, 1998). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. In some embodiments, the DNA binding domain comprises SEQ ID NO:4 or SEQ ID NO:10 or a substantially (e.g., at least 60%, 70%, 80%, 90%, or 95%) identical sequence thereof. A variety of mutations in the Sso7 binding domain have been described in, e.g., US Patent Application Nos. 2005/0048530 and 2007/0141591.

Additional DNA binding domains suitable for use in the invention can be identified by homology with known DNA binding proteins and/or by antibody crossreactivity, or may be found by means of a biochemical assay. DNA binding domains may be synthesized or isolated using the techniques described herein and known in the art.

Sequence non-specific doubled-stranded nucleic acid binding domains for use in the invention can also be identified by cross-reactivity using antibodies, including but not limited to polyclonal antibodies, that bind to known nucleic acid binding domains. Polyclonal antibodies are generated using methods well known to those of ordinary skill in the art (see, e.g., Coligan, Current Protocols in Immunology (1991); Harlow & Lane, Antibodies, A Laboratory Manual (1988)). Those proteins that are immunologically cross-reactive binding proteins can then be detected by a variety of assay methods. For descriptions of various formats and conditions that can be used, see, e.g., Methods in Cell Biology: Antibodies in Cell Biology, volume 37 (Asai, ed. 1993), Coligan, supra, and Harlow & Lane, supra.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radio-labeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain suitable for use in the invention binds to double-stranded nucleic acids in a sequence-independent fashion, i.e., a binding domain of the invention binds double-stranded nucleic acids with a significant affinity, but, there is no known nucleic acid that binds to the domain with more than 100-fold more affinity than another nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific double-stranded nucleic acid binding domains for use in the invention can also be assessed, for example, by assaying the ability of the double-stranded binding domain to increase processivity or efficiency of a modifying enzyme or to increase the stability of a nucleic acid duplex by at least 1° C. can be determined.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_m$ of the double-stranded substrate can be determined from the midpoint of the melting curve. The effect of the sequence-non-specific double-stranded nucleic-acid-binding protein on the $T_m$ can then be determined by comparing the $T_m$ obtained in the presence of the modified enzyme with that in the presence of the unmodified enzyme. (The protein does not significantly contribute to the UV absorbance because it has a much lower extinction coefficient at 260 nm than DNA). A domain that increases the $T_m$ by 1° C., often by 5° C., 10° C. or more, can then be selected for use in the invention.

Novel sequence non-specific double-stranded nucleic acid binding proteins of the invention can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

Conjugating Polymerases to Nucleic Acid Binding Domains

A DNA polymerase of the present invention (e.g., SEQ ID NO2 or a variant thereof) can be joined to a sequence non-specific DNA binding domain by methods well known to those of skill in the art. These methods include both chemical and recombinant means.

Chemical linking of the DNA polymerase to the non-specific DNA binding domain can be performed, for example, as described in Bioconjugate Techniques, Hermanson, Ed., Academic Press (1996). Joining can include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

Linking the DNA polymerase to the non-specific DNA binding domain may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) J. Am. Chem. Soc., 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, Proteins Structures and Molecular Principles, 50-60 (1983)). The composition of the synthetic polypeptides or of subfragments of the polypeptide, may be confirmed by amino acid analysis or sequencing (e.g., the Edman degradation procedure; see Creighton, Proteins, Structures and Molecular Principles, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N-methyl amino acids, and amino acid analogs in general. Furthermore, the amino acid can be D (dextrorotary) or L (levorotary).

In another embodiment, the DNA polymerase and the non-specific DNA binding domain are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

Alternatively, in some embodiments, the coding sequences of each polypeptide in the hybrid polymerase are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of linking the DNA polymerase and the non-specific DNA binding domain include ionic binding by expressing negative and positive tails and indirect binding through antibodies and streptavidin-biotin interactions. (See, e.g., Bioconjugate Techniques, supra). The domains may also be joined together through an intermediate interacting sequence. For example, an Sso7d-interacting sequence, i.e., a sequence that binds to Sso7d, can be joined to a polymerase. The resulting fusion protein can then be allowed to associate non-covalently with the Sso7d to generate an Sso7d-polymerase conjugate.

In some embodiments, a hybrid polymerase of the invention is produced by recombinant expression of a nucleic acid encoding the protein. Such a hybrid polymerase can be made by ligating the appropriate nucleic acid sequences encoding the desired amino acid sequences to each other by methods known in the art, in the proper coding frame, and expressing the product by methods known in the art.

Nucleic acids encoding the domains to be incorporated into the hybrid polymerases of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Nucleic acid sequences that encode the DNA polymerase and the non-specific DNA binding domain polypeptides can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the Sso7 and polymerase sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes.

In an example of obtaining a nucleic acid encoding a DNA polymerase or non-specific DNA binding domain using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Exemplary hybrid polymerases of the present invention include, for example, polymerases having the amino acid sequence of SEQ ID NO:5 or polymerases comprising an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

Assays to Evaluate Polymerase Activity

Activity of a polymerase can be measured using a variety of assays that can be used to determine processivity or modification activity of a polymerase. Improvement in activity may include both increased processivity and increased efficiency.

The polymerases of the present invention, e.g., SEQ ID NO:5, exhibit polymerase activity, e.g., processivity, primer/template binding specificity, and 3' to 5' exonuclease activity. The activities can be measured using techniques that are standard in the art.

For example, polymerase processivity can be measured by a variety of methods known to those of ordinary skill in the art. Polymerase processivity is generally defined as the number of nucleotides incorporated during a single binding event of a modifying enzyme to a primed template. For example, a 5' FAM-labeled primer is annealed to circular or linearized ssM13mp18 DNA to form a primed template. In measuring processivity, the primed template usually is present in significant molar excess to the polymerase so that the chance of any primed template being extended more than once by the polymerase is minimized. The primed template is therefore mixed with the polymerase at a ratio such as approximately 4000:1 (primed DNA:DNA polymerase) in the presence of buffer and dNTPs. MgCl$_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a protein of the invention, e.g., SEQ ID NO:2 or SEQ ID NO:5, is then compared to the processivity of a wild type enzyme.

Efficiency can be demonstrated by measuring the ability of an enzyme to produce product. Increased efficiency can be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12 nucleotide in length, primer annealed at an elevated temperature, e.g., 50° C. In this analysis, enhanced efficiency is shown by the ability of a polymerase to produce more product in a PCR reaction using the 12 nucleotide primer annealed at 50° C.

Efficiency can also be measured, e.g., in a real-time PCR. The Ct value represents the number of cycles required to generate a detectable amount of DNA (a "detectable" amount of DNA is typically 2×, usually 5×, 10×, 100× or more above background). An efficient polymerase may be able to produce a detectable amount of DNA in a smaller number of cycles by more closely approaching the theoretical maximum amplification efficiency of PCR. Accordingly, a lower Ct value reflects a greater amplification efficiency for the enzyme.

Long PCR may be used as another method of demonstrating enhanced efficiency. For example, an enzyme with enhanced efficiency typically allows the amplification of a long amplicon (>5 kb) in a shorter extension time compared to an enzyme with relatively lower efficiency.

Assays such as salt sensitivity can also be used to demonstrate improvement in efficiency or equivalent efficiency of a polymerase of the invention. A polymerase of the present invention may exhibit increased tolerance to high salt concentrations, i.e., a processive enzyme with increased processivity can produce more product in higher salt concentrations. For example, a PCR analysis can be performed to determine the amount of product obtained in a reaction using a polymerase of the present invention compared to a wild type polymerase in reaction conditions with high salt, e.g., 80 mM.

Other methods of assessing efficiency of the polymerases of the invention can be determined by those of ordinary skill in the art using standard assays of the enzymatic activity of a given modification enzyme.

Primer/template specificity is the ability of an enzyme to discriminate between matched primer/template duplexes and mismatched primer/template duplexes. Specificity can be determined, for example, by comparing the relative yield of two reactions, one of which employs a matched primer, and one of which employs a mismatched primer. An enzyme with increased discrimination will have a higher relative yield with the matched primer than with the mismatched primer, i.e., the ratio of the yield in the reaction using the matched primer vs. the reaction using the mismatched primer is about 1 or above. This ratio can then be compared to the yield obtained in a parallel set of reactions employing a wild type polymerase.

Producing Polymerases

Polymerases of the invention can be produced using techniques known in the art. Nucleic acids encoding the polymerase, and optionally linked to a DNA binding domain can be obtained using routine techniques in the field of recombinant genetics. An exemplary nucleic acid encoding SEQ ID NO:2 is provided as SEQ ID NO:1. Depending on the host cell in which the polymerase is to be expressed, codon optimization can be employed to optimize expression of the polymerase in a particular host cell. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117, each of which is incorporated by reference in its entirety for all purposes and in particular for all teachings related to amplification methods.

One of skill will recognize that modifications can additionally be made to the polymerases of the present invention without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The polymerases of the present invention can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, Gene Expression in Recombinant Microorganisms (Bioprocess Technology, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus,* and *Pyricularia*. See, e.g., U.S. Pat. No. 5,679,543 and Stahl and Tudzynski, Eds., Molecular Biology in Filamentous Fungi, John Wiley & Sons, 1992. Synthesis of heterologous proteins in yeast is well known and described in the literature. Methods in Yeast Genetics, Sherman, F., et al., Cold Spring Harbor Laboratory, (1982) is a well recognized work describing the various methods available to produce the enzymes in yeast.

There are many expression systems for producing the polymerase polypeptides of the present invention that are well known to those of ordinary skill in the art. (See, e.g., Gene Expression Systems, Fernandex and Hoeffler, Eds. Academic Press, 1999; Sambrook and Russell, supra; and Ausubel et al, supra.) Typically, the polynucleotide encoding the polymerase is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived PL promoter and N-gene ribosome binding site (Shimatake et al., Nature (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, lambda-phage derived vectors, and fusion expression systems such as GST and LacZ. Epitope tags can also be added to recombinant proteins to provide convenient methods of isolation, e.g., c-myc, HA-tag, 6-His (SEQ ID NO:15) tag, maltose binding protein, VSV-G tag, anti-DYKDDDDK (SEQ ID NO:16) tag, or any such tag, a large number of which are well known to those of skill in the art.

For expression in prokaryotic cells other than E. coli, a promoter that functions in the particular prokaryotic species is required. Such promoters can be obtained from genes that have been cloned from the species, or heterologous promoters can be used. For example, the hybrid trp-lac promoter functions in Bacillus sp. in addition to E. coli. These and other suitable bacterial promoters are well known in the art and are described, e.g., in Sambrook et al. and Ausubel et al. Bacterial expression systems for expressing the proteins of the invention are available in, e.g., E. coli, Bacillus sp., and Salmonella (Palva et al., Gene 22:229-235 (1983); Mosbach et al., Nature 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For E. coli and other bacterial host cells, inducible promoters are known to those of skill in the art. These include, for example, the lac promoter, the bacteriophage lambda $P_L$ promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al. (1985) Proc. Nat'l Acad. Sci. USA 82: 1074-8). These promoters and their use are also discussed in Sambrook et al., supra.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), J. Biol. Chem. 263: 16297-16302.

The construction of polynucleotide constructs can involve the use of vectors able to replicate in bacteria. Such vectors are commonly used in the art. A plethora of kits are commercially available for the purification of plasmids from bacteria (for example, EasyPrep™, FlexiPrep™, from Pharmacia Biotech; StrataClean™, from Stratagene; and, QIAexpress® Expression System, Qiagen). The isolated and purified plasmids can then be further manipulated to produce other plasmids, and used to transform cells.

The polypeptides of the invention can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2: 800; Schoner et al., Bio/Technology (1985) 3: 151). Polypeptides of the invention can be expressed in a variety of host cells, including E. coli, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). In some embodiments, substantially pure compositions of at least about 90 to 95% homogeneity are preferred, and 98 to 99% or more homogeneity are most preferred. Once purified, partially or to homogeneity as desired, the polypeptides may then be used (e.g., in DNA amplification).

To facilitate purification of the polypeptides of the invention, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad, Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester, N.Y.)). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilotri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

One of skill in the art will recognize that after biological expression or purification, the polymerase conjugates(s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem. 268: 14065-14070; Kreitman and Pastan (1993) Bioconjug. Chem. 4: 581-585; and Buchner et al. (1992) Anal. Biochem. 205: 263-270). Debinski et al., for example, describe the denaturation and reduction of inclusion body proteins in guanidine-DTE. The protein is then refolded in a redox buffer containing oxidized glutathione and L-arginine.

III. Methods

In another aspect, the present invention provides for methods of amplifying a target nucleic acid using a polymerase of the invention (e.g., a polypeptide comprising a DNA polymerase having an amino acid sequence at least 95% (or at least 96%, at least 97%, at least 98%, or at least 99%) identical to SEQ ID NO:2 or a polymerase linked to a sequence non-specific DNA binding domain). Such amplification reactions include without limitation the polymerase chain reaction (PCR). Polymerase chain reactions that can be conducted using the compositions described herein include, without limitation, reverse-transcription PCR (rt-PCR) and quantitative PCR (qPCR).

In some embodiments, the methods of the present invention are useful for amplifying a long amplicon, e.g., an amplicon of at least 5 kb, at least 7 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb. In some embodiments, the methods of amplifying a target nucleic acid using a polymerase of the invention (e.g., a polypeptide comprising a DNA polymerase having an amino acid sequence at least 95% (or at least 96%, at least 97%, at least 98%, or at least 99%) identical to SEQ ID NO:2 or a polymerase linked to a sequence non-specific DNA binding domain) result in a higher efficiency for amplification of an amplicon of at least 5 kb, at least 7 kb, at least 10 kb, at least 12 kb, at least 15 kb, at least 17 kb, at least 20 kb, at least 22 kb, at least 25 kb, at least 27 kb, at least 30 kb, at least 35 kb, or at least 40 kb as compared to a DNA polymerase consisting of SEQ ID NO:7 or SEQ ID NO:8.

The amplification methods of the present invention using polymerases (e.g., a polypeptide comprising a DNA polymerase having an amino acid sequence at least 95% (or at least 96%, at least 97%, at least 98%, or at least 99%) identical to SEQ ID NO:2 or a polymerase linked to a sequence non-specific DNA binding domain) are carried out using reaction mixtures that are sufficient for amplifying a nucleic acid molecule. In some embodiments, an amplification reaction mixture comprises, in addition to the DNA polymerase or hybrid polymerase, one or more of the following components: nucleotide triphosphates, one or more oligonucleotide primers, salt, buffer, water, stabilizer, and DNA-binding dye.

In some embodiments, the amplification methods of the present invention comprise using polymerases (e.g., a polypeptide comprising a polype DNA polymerase ptide having an amino acid sequence at least 95% (or at least 96%, at least 97%, at least 98%, or at least 99%) identical to SEQ ID NO:2 or a polymerase linked to a sequence non-specific DNA binding domain) with an agent that improves amplification specificity, for example an agent selected from arginine, spermidine, and spermine. In some embodiments, an amplification reaction mixture comprises, in addition to the DNA polymerase or hybrid polymerase, one or more of the following components: nucleotide triphosphates, one or more oligonucleotide primers, salt, buffer, water, stabilizer, and DNA-binding dye; and an agent selected from arginine, spermidine, or spermine.

In some embodiments, an amplification reaction mixture of the present invention comprises: a polymerase (e.g., a polypeptide comprising a DNA polymerase having an amino acid sequence at least 95% (or at least 96%, at least 97%, at least 98%, or at least 99%) identical to SEQ ID NO:2 or a polymerase linked to a sequence non-specific DNA binding domain) as described herein at a concentration of about 1 U/ml to about 75 U/ml (e.g., about 1 U/ml, 5 U/ml, 10 U/ml, 15 U/ml, 20 U/ml, 25 U/ml, 30 U/ml, 35 U/ml, 40 U/ml, 45 U/ml, 50 U/ml, 55 U/ml, 60 U/ml, 65 U/ml, 70 U/ml, or 75 U/ml); dNTPs at a concentration of about 0.1 mM to about 10 mM (e.g., about 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, or 10 mM); magnesium, e.g., $MgCl_2$, at a concentration of about 1 mM to about 20 mM (e.g., about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM); $(NH_4)_2SO_4$ at a concentration of about 10 mM to about 100 mM (e.g., about 10 mM, 20 mM, 30 mM, 40 mM, 50 mM, 60 mM, 70 mM, 80 mM, 90 mM, or 100 mM); potassium, e.g, KCl, at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); a buffer, e.g., Tris pH 8.5-9.5 at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); a disaccharide, e.g., trehalose, at a concentration of about 100 mM to about 500 mM (e.g., about 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, or 500 mM); one or more osmolytes, e.g, sarcosine, trimethylamine N-oxide (TMAO), dimethylsulfoniopropionate, and trimethylglycine, at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); Tween-20 at a concentration of about 0.1% to about 0.5% (e.g., about 0.1%, 0.2%, 0.3%, 0.4%, or 0.5%); glycerol at a concentration of about 1% to about 5% (e.g., about 1%, 2%, 3%, 4%, or 5%); DMSO at a concentration of about 1% to about 10% (e.g., about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%); fluorescein at a concentration of about 0.001% to about 0.01% (e.g., about 0.001%, 0.002%, 0.003%, 0.004%, 0.005%, 0.006%, 0.007%, 0.008%, 0.009%, or 0.01%); DNA binding dye (e.g., cyanine dye) at a concentration of about 0.5× to about 5× (e.g., about 0.5×, 0.6×, 0.7×, 0.8×, 0.9×, 1×, 1.5×, 2×, 2.5×, 3×, 3.5×, 4×, 4.5×, or 5×); and optionally arginine, spermidine, or spermine or a salt thereof at a concentration of about 1 mM to about 100 mM (e.g., about 1 mM, 5 mM, 10 mM, 15 mM, 20 mM, 25 mM, 30mM, 35 mM, 40 mM, 45 mM, 50 mM, 55 mM, 60 mM, 65 mM, 70 mM, 75 mM, 80 mM, 85 mM, 90 mM, 95 mM, or 100 mM).

Improvements in efficiency and specificity due to certain aspects of the present invention can be identified and quantified using assays known in the art and described in further detail below.

In some embodiments, dye-based qPCR detection methods are used to monitor amplification reactions utilizing components of the invention. Such detection methods generally rely on monitoring the increase in fluorescence signal due to the binding of DNA-binding dye to the amplified DNA. For example, SYBR Green I, a commonly used fluorescent DNA binding dye, binds all double-stranded DNA and detection is monitored by measuring the increase in fluorescence throughout the cycle. SYBR Green I has an excitation and emission maxima of 494 nm and 521 nm, respectively.

In other embodiments, probe-based qPCR detection methods are used to monitor amplification reactions utilizing components of the invention. Such detection methods generally rely on the sequence-specific detection of a desired PCR product. Unlike dye-based qPCR methods that detect all double-stranded DNA, probe-based qPCR utilizes a fluorescent-labeled target-specific probe, which detects specific sequences in the amplified DNA.

In certain aspects, it may be desirable to include an additional compound as an additive to improve efficiency in amplification reactions, including but not limited to qPCR. In some embodiments, inclusion of the additive is sufficient to increase efficiency of the polymerase conjugate by at least 5, 10, 15, 20, 25, 35, 40, or 50% or more compared to a control mixture lacking the additive.

In some embodiments, a polymerase conjugate of the invention exhibits low efficiency for certain targets when used in a formulation that includes certain binding dyes (such as, for example, an EvaGreen DNA binding dye). Such low efficiency may in some embodiments result in a delay of Ct values associated with low input DNA concentrations. Methods for measuring efficiency of a particular reaction are known in the art and described in further detail below.

In some embodiments, the additive is an osmolyte included in an amplification reaction of the invention to improve efficiency. Members of the osmolyte family have been shown to improve the thermal stability of proteins (Santoro, Biochemistry, 1992) as well as decrease DNA double helix stability (Chadalavada, FEBS Letters, 1997). In some embodiments, osmolytes are small molecules or compounds which are produced by living organisms in response to environmental stresses such as extreme temperatures, dehydration, or salinity and which protect their cellular components and help to maintain optimal cytosolic conditions. Osmolytes of use in the present invention may include without limitation sarcosine, trimethylamine N-oxide (TMAO), dimethylsulfoniopropionate, and trimethylglycine. Sarcosine is chemically similar to betaine, a chemical which has been shown to improve conventional PCR (Henke, Nucleic Acids Research, 1997).

In conventional uses of osmolytes, the stabilizing effects of such compounds are generally observed at relatively high concentrations (>1M). However, in methods of the present invention, millimolar concentrations of osmolytes have been found to be effective for improving the reaction efficiency of amplification reactions such as qPCR. Without being bound by a mechanism of action, it is possible that the improvement in efficiency is the result of improving the accessibility of the DNA polymerase to the targeted region of the DNA template for reactions that contain low concentrations of input DNA sample. In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, and about 300 to about 350 mM osmolytes are used in methods and kits of the invention. In some embodiments, the osmolyte used in methods, reaction mixtures, and kits of the invention is sarcosine (optionally at the above-listed concentrations).

IV. Reaction Mixtures

In another aspect, the present invention provides reaction mixtures comprising a polymerase of the invention. In some embodiments, a reaction mixture comprises a DNA polymerase having the amino acid sequence of SEQ ID NO:2 or a DNA polymerase comprising an amino acid sequence that is at least 95% (or at least 96%, at least 97%, at least 98%, or at least 99%) identical to SEQ ID NO:2. In some embodiments, a reaction mixture comprises a polypeptide comprising a DNA polymerase having an amino acid sequence at least 95% identical to SEQ ID NO:2 linked to a non-specific DNA binding domain, e.g., a non-specific DNA binding domain comprising an amino acid sequence that is at least 80% identical to SEQ ID NO:4 or SEQ ID NO:10. In some embodiments, a reaction mixture comprises a polypeptide having the amino acid sequence of SEQ ID NO:5 or a polypeptide comprising an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

The reaction mixture can further comprise one or more reagents for amplification of a target nucleic acid, including but not limited to a target nucleic acid, one or more oligonucleotides, buffers, nucleotide triphosphates, salts, stabilizers, one or more additives for improving efficiency, nuclease-free water, and/or a double stranded DNA binding dye.

In some embodiments, the reaction mixture can comprise a sufficient amount of an agent to improve the specificity of nucleic acid amplification. For example, in some embodiments, the agent is selected from arginine (e.g., L-arginine or D-arginine), spermidine, and spermine, or a salt thereof. In some embodiments, the reaction mixture can comprise an additional compound as an additive to improve efficiency in amplification reactions. In some embodiments, the additive is an osmolyte, including but not limited to sarcosine, trimethylamine N-oxide (TMAO), dimethylsulfoniopropionate, or trimethylglycine.

V. Kits

In another aspect, the present invention provides kits for conducting nucleic acid amplification reactions. The kits include a polymerase of the invention (e.g., a polypeptide comprising a DNA polymerase having an amino acid sequence at least 95% identical to SEQ ID NO:2, or a polypeptide comprising a DNA polymerase having an amino acid sequence at least 95% identical to SEQ ID NO:2 linked to a non-specific DNA binding domain). In some embodiments, a kit comprises a DNA polymerase having the amino acid sequence of SEQ ID NO:2 or a DNA polymerase comprising an amino acid sequence that is at least 95% (or at least 96%, at least 97%, at least 98%, or at least 99%) identical to SEQ ID NO:2. In some embodiments, a kit comprises a polypeptide having the amino acid sequence of SEQ ID NO:5 or a polypeptide comprising an amino acid sequence that is at least 80% (or at least 85%, at least 90%, at least 91%, at least 92%, at least 93%, at least 94%, at least 95%, at least 96%, at least 97%, at least 98%, or at least 99%) identical to SEQ ID NO:5.

Optionally, the kits comprise one or more dNTPs, at least one buffer, and/or a double stranded DNA binding dye. Such kits may also include stabilizers and other additives (e.g., sarcosine) to increase the efficiency of the amplification reactions. Such kits may also include one or more primers as well as instructions for conducting nucleic acid amplification reactions using the components of the kits. Optionally, the kit can further comprise a sufficient amount of an agent to improve the specificity of nucleic acid amplification. For example, in some embodiments, the agent is selected from arginine (e.g., L-arginine or D-arginine), spermidine, and spermine, or a salt thereof.

EXAMPLES

The following examples are offered to illustrate, but not to limit the claimed invention.

Example 1

Lysates from 96 clones from a library of hybrid polymerase variants were tested for DNA polymerase activity, 3'-5' exonuclease activity and level of protein expression. Clones exhibiting >1 ratio of polymerase activity over exonuclease activity were selected for further purification and characterizations. Among the several clones tested in PCR using equal units of purified enzymes, a variant designated "H10" exhibited improved ability to amplify long amplicons (20 kb). See, FIG. 1. Similar results were observed for 7.5 kb amplicons, with variant H10 producing a noticeably more 7.5 kb product than a control hybrid polymerase (SEQ ID NO:8).

A polymerase fidelity test was performed on H10 along with Taq polymerase and a control hybrid polymerase (SEQ ID NO:8). The results show that H10 has significantly higher fidelity compare to Taq DNA polymerase, and has comparable or slightly higher fidelity than a previously characterized hybrid polymerase clone.

The amino acid sequence of H10 (SEQ ID NO:5) is made up of a polymerase sequence (SEQ ID NO:2) and a sequence non-specific DNA binding domain (SEQ ID NO:4). FIG. 2 illustrates an alignment of the polymerase sequence of H10 with the polymerase sequence of the control hybrid polymerase. Without intending to Emil the scope of the invention, one or more of the differences in the amino acid sequences of the two polymerases are believed to result in the increased efficiency observed in the H10 variant compared to the control.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polypeptide comprising a DNA polymerase having an amino acid sequence at least 97% identical to SEQ ID NO:2.

2. The polypeptide of claim 1, wherein the DNA polymerase comprises SEQ ID NO:2.

3. The polypeptide of claim 1, wherein the DNA polymerase is linked to a non-specific DNA binding domain.

4. The polypeptide of claim 3, wherein the DNA polymerase linked to the non-specific DNA binding domain has higher efficiency for amplification of an amplicon of at least 7.5 kb as compared to a DNA polymerase consisting of SEQ ID NO:8.

5. The polypeptide of claim 3, wherein the non-specific DNA binding domain comprises an amino acid sequence at least 85% identical to SEQ ID NO:4.

6. The polypeptide of claim 3, wherein the non-specific DNA binding domain comprises SEQ ID NO:4.

7. The polypeptide of claim 1, wherein the polypeptide is at least 97% identical to SEQ ID NO:5.

8. The polypeptide of claim 1, wherein the polypeptide comprises SEQ ID NO:5.

* * * * *

SEQUENCE LISTING

```
<160> NUMBER OF SEQ ID NOS: 17

<210> SEQ ID NO 1
<211> LENGTH: 2327
<212> TYPE: DNA
<213> ORGANISM: Artificial Sequence
<220> FEATURE:
<223> OTHER INFORMATION: synthetic exemplary DNA polymerase

<400> SEQUENCE: 1
atgatcctgg atgctgacta catcactgaa gaaggcaaac cggttatccg tctgttcaaa      60
aaagagaacg gcaaatttaa gattgagcat gatcgcacct ttcgtccata catttacgct     120
ctgctgaaag atgattctaa gattgatgaa gttagaaaaa tcactggtga gcgccatggc     180
aagattgttc gtatcgttga tgcggaaaag gtagaaaaga aatttctggg cagaccaatc     240
gaggtgtgga aactgtatct cgaacatcca caagatgttc cggctattcg cgataaagtt     300
cgcgaacatc ctgcagttgt tgacatcttc gaatacgata ttccatttgc aaagcgttac     360
ctcatcgaca aaggcctgat accaatggag ggcgaggaag aactcaagat cctggcgttc     420
gatatagaaa ccctctatca cgaaggcgaa gagtttggta aaggcccaat tataatgatc     480
agctatgcag atgaaaacga agcaaggtg attacttgga aaaacataga tctcccatac     540
gttgaggttg tatcttccga gcgcgagatg attaagcgct ttctcagagt tatccgcgag     600
aaggatccgg acgttatcat tacttataac ggcgactctt ttgacttccc atatctggtg     660
aaacgcgcag aaaaactcgg tattaaactg actatcggcc gtgatggttc cgagccgaag     720
atgcagcgtc tcggcgatat gaccgctgta gaaattaagg tcgtatcca tttcgacctg     780 tatcatgtaa ttcgtcgtac tattaacctc ccgacttaca ctctcgaggc tgtatatgaa     840
```

```
gcaatttttg gtaagccgaa ggagaaggta tacgccgatg agattgcaga ggcgtgggaa    900
tccggtgagg gcctcgagcg tgttgcaaaa tactccatgg aagatgcaaa ggtgacttat    960
gaactcggca agaattcct cccaatggaa atccagctct ctcgcctggt tggccaacca   1020
ctgtgggatg tttctcgttc ttccaccggt aacctcgtag agtggtttct cctgcgcaaa   1080
gcgtacgaac gcaacgaagt ggctccgaac aagccatctg aagaagagta tgaacgccgt   1140
ctccgcgagt cttacgctgg tggctatgtt aaagagccag aaaagggcct ctgggaaaac   1200
atcgtgtccc tcgattttcg ctctctgtat ccgtctatta tcattaccca caacgtgtct   1260
ccggatactc tcaaccgcga gggctgcaga gagtatgata ttgctccgga agtaggccac   1320
aagttctgca aggacttccc gggctttatt ccgtctctcc tgaaacatct gctcgaggaa   1380
cgccaaaaga ttaagactaa aatgaaggag tcccaggatc cgattgaaaa aaaaatgctc   1440
gactatcgcc aaagagcgat taaaatcctc gcaaactctt tttacggcta ttatggctat   1500
gcaaaagcac gctggtactg taaggagtgt gctgagtccg ttactgcttg gggtcgcaaa   1560
tacatcgagt tcgtgtggaa ggagctcgaa gaaagtttg gctttaaagt tctctacatt   1620
gacactgatg gtctctatgc gactattccg ggtggtgagc ctgaggaaat taagaaaaag   1680
gctctagaat ttgtgaaata cattaactcg aagctcccgg gtctcctgga gctcgaatat   1740
gaaggctttt atgttcgcgg cttcttcgtt accaagaaga gatatgcggt gattgatgaa   1800
gaaggcaaag ttattactcg tggtctcgag attgtgcgcc gtgattggag cgaaattgcg   1860
aaagaaactc aagctagagt tctcgagact attctcaaac acggcaacgt tgaagaagct   1920
gtgaaaattg taaagaagt aacccaaaag ctcgctaact atgaaattcc gccagagaag   1980
ctcgcgattt atgagcagat tactcgcccg ctgcatgagt ataaggcgat tggtccgcac   2040
gtggctgttg caaagaaact ggctgctaga ggcgtgaaaa ttaaaccggg tatggtaatt   2100
ggctacattg tactccgcgg cgatggtccg attagcaaac gtgcaattct agctgaggaa   2160
ttcgatccga gaaagcacaa gtatgacgca gaatattaca ttgagaacca ggtgctcccg   2220
gcggtactcc gtattctgga gggttttggc taccgtaagg aagacctccg ctggcaaaag   2280
actaaacagg ttggcctcac ttcttggctc aacattaaaa aatccgg           2327
```

<210> SEQ ID NO 2
<211> LENGTH: 775
<212> TYPE: PRT
<213> ORGANISM: Artificial Sequence
<220> FEATURE:
<223> OTHER INFORMATION: synthetic exemplary DNA polymerase

<400> SEQUENCE: 2

```
Met Ile Leu Asp Ala Asp Tyr Ile Thr Glu Glu Gly Lys Pro Val Ile
 1               5                  10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Asp Glu Val Arg Lys Ile Thr Gly Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Val Arg Glu His Pro Ala Val Val Asp Ile Phe Glu Tyr
```

```
                100               105                 110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
            180                 185                 190
Arg Phe Leu Arg Val Ile Arg Glu Lys Asp Pro Asp Val Ile Ile Thr
            195                 200                 205
Tyr Asn Gly Asp Ser Phe Asp Phe Pro Tyr Leu Val Lys Arg Ala Glu
        210                 215                 220
Lys Leu Gly Ile Lys Leu Thr Ile Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Glu Ala Trp Glu Ser Gly Glu Gly
        290                 295                 300
Leu Glu Arg Val Ala Lys Tyr Ser Met Glu Asp Ala Lys Val Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Tyr Glu Arg Arg Leu Arg Glu Ser
        370                 375                 380
Tyr Ala Gly Gly Tyr Val Lys Glu Pro Glu Lys Gly Leu Trp Glu Asn
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Ile Ala Pro Glu Val Gly His Lys Phe Cys Lys Asp Phe Pro Gly
            435                 440                 445
Phe Ile Pro Ser Leu Leu Lys His Leu Leu Glu Arg Gln Lys Ile
        450                 455                 460
Lys Thr Lys Met Lys Glu Ser Gln Asp Pro Ile Glu Lys Lys Met Leu
465                 470                 475                 480
Asp Tyr Arg Gln Arg Ala Ile Lys Ile Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Phe Val Trp Lys Glu
            515                 520                 525
```

-continued

Leu Glu Glu Lys Phe Gly Phe Lys Val Leu Tyr Ile Asp Thr Asp Gly
530                 535                 540

Leu Tyr Ala Thr Ile Pro Gly Gly Glu Pro Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asn Val Glu Ala
625                 630                 635                 640

Val Lys Ile Val Lys Glu Val Thr Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Arg Gly Val Lys Ile Lys Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Val Gly Leu Thr Ser
            755                 760                 765

Trp Leu Asn Ile Lys Lys Ser
770                 775

<210> SEQ ID NO 3
<211> LENGTH: 6
<212> TYPE: PRT
<213> ORGANISM: Artificial Sequence
<220> FEATURE:
<223> OTHER INFORMATION: synthetic flexible peptide linker

<400> SEQUENCE: 3

Gly Thr Gly Gly Gly Gly
 1               5

<210> SEQ ID NO 4
<211> LENGTH: 63
<212> TYPE: PRT
<213> ORGANISM: Artificial Sequence
<220> FEATURE:
<223> OTHER INFORMATION: synthetic exemplary non-specific DNA binding
      domain

<400> SEQUENCE: 4

Ala Thr Val Lys Phe Lys Tyr Lys Gly Glu Glu Lys Glu Val Asp Ile
 1               5                  10                  15

Ser Lys Ile Lys Lys Val Trp Arg Val Gly Lys Met Ile Ser Phe Thr
                20                  25                  30

Tyr Asp Glu Gly Gly Gly Lys Thr Gly Arg Gly Ala Val Ser Glu Lys
            35                  40                  45

```
Asp Ala Pro Lys Glu Leu Leu Gln Met Leu Glu Lys Gln Lys Lys
    50                  55                  60

<210> SEQ ID NO 5
<211> LENGTH: 844
<212> TYPE: PRT
<213> ORGANISM: Artificial Sequence
<220> FEATURE:
<223> OTHER INFORMATION: synthetic exemplary hybrid DNA polymerase
      comprising non-specific DNA binding domain

<400> SEQUENCE: 5

Met Ile Leu Asp Ala Asp Tyr Ile Thr Glu Gly Lys Pro Val Ile
 1               5                  10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Lys Asp Asp Ser Lys Ile
                35                  40                  45

Asp Glu Val Arg Lys Ile Thr Gly Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Val Ile Arg Glu Lys Asp Pro Asp Val Ile Ile Thr
        195                 200                 205

Tyr Asn Gly Asp Ser Phe Asp Phe Pro Tyr Leu Val Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Glu Ala Trp Glu Ser Gly Glu Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350
```

```
Val Glu Trp Phe Leu Leu Arg Lys Ala Tyr Glu Arg Asn Glu Val Ala
            355                 360                 365

Pro Asn Lys Pro Ser Glu Glu Tyr Glu Arg Arg Leu Arg Glu Ser
        370                 375                 380

Tyr Ala Gly Gly Tyr Val Lys Glu Pro Glu Lys Gly Leu Trp Glu Asn
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Ile Ala Pro Glu Val Gly His Lys Phe Cys Lys Asp Phe Pro Gly
            435                 440                 445

Phe Ile Pro Ser Leu Leu Lys His Leu Leu Glu Arg Gln Lys Ile
        450                 455                 460

Lys Thr Lys Met Lys Glu Ser Gln Asp Pro Ile Glu Lys Lys Met Leu
465                 470                 475                 480

Asp Tyr Arg Gln Arg Ala Ile Lys Ile Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Phe Val Trp Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Pro Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asn Val Glu Glu Ala
625                 630                 635                 640

Val Lys Ile Val Lys Glu Val Thr Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Arg Gly Val Lys Ile Lys Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Val Gly Leu Thr Ser
        755                 760                 765

Trp Leu Asn Ile Lys Lys Ser Gly Thr Gly Gly Gly Gly Ala Thr Val
```

```
                770                 775                 780
Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys
                835                 840

<210> SEQ ID NO 6
<211> LENGTH: 2543
<212> TYPE: DNA
<213> ORGANISM: Artificial Sequence
<220> FEATURE:
<223> OTHER INFORMATION: synthetic exemplary hybrid DNA polymerase
      comprising non-specific DNA binding domain
<220> FEATURE:
<221> NAME/KEY: modified_base
<222> LOCATION: (806)...(806)
<223> OTHER INFORMATION: n = g, a, c or t

<400> SEQUENCE: 6
atgatcctgg atgctgacta catcactgaa gaaggcaaac cggttatccg tctgttcaaa      60
aaagagaacg gcaaatttaa gattgagcat gatcgcacct tcgtccata catttacgct     120 ctgctgaaag atgattctaa gattgatgaa gttagaaaaa tcactggtga gcgccatggc     180
aagattgttc gtatcgttga tgcggaaaag gtagaaaaga aatttctggg cagaccaatc     240
gaggtgtgga aactgtatct cgaacatcca caagatgttc cggctattcg cgataaagtt     300
cgcgaacatc ctgcagttgt tgacatcttc gaatacgata ttccatttgc aaagcgttac     360
ctcatcgaca aaggcctgat accaatggag ggcgaggaag aactcaagat cctggcgttc     420
gatatagaaa ccctctatca cgaaggcgaa gagtttggta aaggcccaat tataatgatc     480
agctatgcag atgaaaacga agcaaggtg attacttgga aaaacataga tctcccatac     540
gttgaggttg tatcttccga cgcgagatg attaagcgct ttctcagagt tatccgcgag     600
aaggatccgg acgttatcat tacttataac ggcgactctt ttgacttccc atatctggtg     660
aaacgcgcag aaaaactcgg tattaaactg actatcggcc gtgatggttc cgagccgaag     720
atgcagcgtc tcggcgatat gaccgctgta gaaattaagg gtcgtatcca tttcgacctg     780
tatcatgtaa ttcgtcgtac tattanaacc tcccgactta cactctcgag gctgtatatg     840
aagcaatttt tggtaagccg aaggagaagg tatacgccga tgagattgca gaggcgtggg     900
aatccggtga gggcctcgag cgtgttgcaa aatactccat ggaagatgca aggtgacatt     960
atgaactcgg caagaaattc ctcccaatgg aaatccagct ctctcgcctg gttggccaac    1020
cactgtggga tgtttctcgt tcttccaccg gtaacctcgt agagtggttt ctcctgcgca    1080
aagcgtacga acgcaacgaa gtggctccga caagccatc tgaagaagag tatgaacgcc    1140
gtctccgcga gtcttacgct ggtggctatg ttaaagagcc agaaaagggc ctctgggaaa    1200
acatcgtgtc cctcgatttt cgctctctgt atccgtctat tatcattacc cacaacgtgt    1260
ctccggatac tctcaaccgc gagggctgca gagagtatga tattgctccg gaagtaggcc    1320
acaagttctg caaggacttc ccgggctta ttccgtctct cctgaaacat ctgctcgagg    1380
aacgccaaaa gattaagact aaaatgaagg agtcccagga tccgattgaa aaaaaaatgc    1440
tcgactatcg ccaaagagcg attaaatcc tcgcaaactc ttttacggc tattatggct    1500 atgcaaaagc acgctggtac tgtaaggagt gtgctgagtc cgttactgct tggggtcgca    1560
```

```
aatacatcga gttcgtgtgg aaggagctcg aagaaaagtt tggctttaaa gttctctaca    1620
ttgacactga tggtctctat gcgactattc cgggtggtga gcctgaggaa attaagaaaa    1680
aggctctaga atttgtgaaa tacattaact cgaagctccc gggtctcctg gagctcgaat    1740
atgaaggctt ttatgttcgc ggcttcttcg ttaccaagaa gagatatgcg gtgattgatg    1800
aagaaggcaa agttattact cgtggtctcg agattgtgcg ccgtgattgg agcgaaattg    1860
cgaaagaaac tcaagctaga gttctcgaga ctattctcaa acacggcaac gttgaagaag    1920
ctgtgaaaat tgtaaaagaa gtaacccaaa agctcgctaa ctatgaaatt ccgccagaga    1980
agctcgcgat ttatgagcag attactcgcc cgctgcatga gtataaggcg attggtccgc    2040
acgtggctgt tgcaaagaaa ctggctgcta gaggcgtgaa aattaaaccg gtatggtaa    2100 ttggctacat tgtactccgc ggcgatggtc cgattagcaa acgtgcaatt ctagctgagg    2160
aattcgatcc gagaaagcac aagtatgacg cagaatatta cattgagaac caggtgctcc    2220
cggcggtact ccgtattctg gagggttttg gctaccgtaa ggaagacctc cgctggcaaa    2280
agactaaaca ggttggcctc acttcttggc tcaacattaa aaaatccggt accggcggtg    2340
gcggtgcaac cgtaaagttc aagtacaaag gcgaagaaaa agaggtagac atctccaaga    2400
tcaagaaagt atggcgtgtg ggcaagatga tctccttcac ctacgacgag ggcggtggca    2460
agaccggccg tgtgcggta agcgaaaagg acgcgccgaa ggagctgctg cagatgctgg    2520
agaagcagaa aaagtgagct agc                                            2543

<210> SEQ ID NO 7
<211> LENGTH: 775
<212> TYPE: PRT
<213> ORGANISM: Artificial Sequence
<220> FEATURE:
<223> OTHER INFORMATION: synthetic control DNA polymerase

<400> SEQUENCE: 7

Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190
```

-continued

```
Arg Phe Leu Lys Ile Ile Arg Glu Lys Asp Pro Asp Ile Ile Thr
            195                 200                 205
Tyr Asn Gly Asp Ser Phe Asp Leu Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
    290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Lys Ile
    450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Lys Ser Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
```

```
               610                 615                 620
Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                    645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                    725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
            755                 760                 765

Trp Leu Asn Ile Lys Lys Ser
770                 775

<210> SEQ ID NO 8
<211> LENGTH: 844
<212> TYPE: PRT
<213> ORGANISM: Artificial Sequence
<220> FEATURE:
<223> OTHER INFORMATION: synthetic control hybrid DNA polymerase with
      Sso7d DNA binding domain

<400> SEQUENCE: 8

Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
```

-continued

```
            195                 200                 205
Tyr Asn Gly Asp Ser Phe Asp Leu Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Thr Gly Glu Gly
    290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Phe Val Lys Glu Pro Glu Lys Gly Leu Trp Glu Asn
385                 390                 395                 400
Ile Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Arg Asn Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Lys Ile
    450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Lys Ser Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
```

```
Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
            645                 650                 655

Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Arg Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys
        835                 840

<210> SEQ ID NO 9
<211> LENGTH: 25
<212> TYPE: PRT
<213> ORGANISM: Artificial Sequence
<220> FEATURE:
<223> OTHER INFORMATION: synthetic conserved DNA polymerase sequence

<400> SEQUENCE: 9

Tyr Gly Tyr Tyr Gly Tyr Ala Lys Ala Arg Trp Tyr Cys Lys Glu Cys
1               5                   10                  15

Ala Glu Ser Val Thr Ala Trp Gly Arg
            20                  25

<210> SEQ ID NO 10
<211> LENGTH: 64
<212> TYPE: PRT
<213> ORGANISM: Artificial Sequence
<220> FEATURE:
<223> OTHER INFORMATION: synthetic Ss07d/Ssh7A/SsoP2 DNA binding domain

<400> SEQUENCE: 10

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60
```

```
<210> SEQ ID NO 11
<211> LENGTH: 64
<212> TYPE: PRT
<213> ORGANISM: Sulfolobus shibatae
<220> FEATURE:
<223> OTHER INFORMATION: Ssh7b DNA-binding protein, Sso7-like protein

<400> SEQUENCE: 11

Met Val Thr Val Lys Phe Lys Tyr Lys Gly Glu Glu Lys Glu Val Asp
 1               5                  10                  15

Thr Ser Lys Ile Lys Lys Val Trp Arg Val Gly Lys Met Ile Ser Phe
             20                  25                  30

Thr Tyr Asp Glu Gly Gly Gly Lys Thr Gly Arg Gly Ala Val Ser Glu
         35                  40                  45

Lys Asp Ala Pro Lys Glu Leu Leu Gln Met Leu Glu Lys Gln Lys Lys
     50                  55                  60

<210> SEQ ID NO 12
<211> LENGTH: 66
<212> TYPE: PRT
<213> ORGANISM: Sulfolobus sp.
<220> FEATURE:
<223> OTHER INFORMATION: Sac7d DNA-binding protein, Sso7-like protein

<400> SEQUENCE: 12

Met Val Lys Val Lys Phe Lys Tyr Lys Gly Glu Glu Lys Glu Val Asp
 1               5                  10                  15

Thr Ser Lys Ile Lys Lys Val Trp Arg Val Gly Lys Met Val Ser Phe
             20                  25                  30

Thr Tyr Asp Asp Asn Gly Lys Thr Gly Arg Gly Ala Val Ser Glu Lys
         35                  40                  45

Asp Ala Pro Lys Glu Leu Leu Asp Met Leu Ala Arg Ala Glu Arg Glu
     50                  55                  60

Lys Lys
65

<210> SEQ ID NO 13
<211> LENGTH: 65
<212> TYPE: PRT
<213> ORGANISM: Sulfolobus acidocaldarius
<220> FEATURE:
<223> OTHER INFORMATION: Sulfolobus acidocaldarius DSM 639 Sac7e
      DNA-binding protein, Sso7-like protein

<400> SEQUENCE: 13

Met Ala Lys Val Arg Phe Lys Tyr Lys Gly Glu Glu Lys Glu Val Asp
 1               5                  10                  15

Thr Ser Lys Ile Lys Lys Val Trp Arg Val Gly Lys Met Val Ser Phe
             20                  25                  30

Thr Tyr Asp Asp Asn Gly Lys Thr Gly Arg Gly Ala Val Ser Glu Lys
         35                  40                  45

Asp Ala Pro Lys Glu Leu Met Asp Met Leu Ala Arg Ala Glu Lys Lys
     50                  55                  60

Lys
65

<210> SEQ ID NO 14
<211> LENGTH: 64
<212> TYPE: PRT
<213> ORGANISM: Sulfolobus tokodaii
<220> FEATURE:
<223> OTHER INFORMATION: Sulfolobus tokodaii strain 7 Sto7e DNA-binding
``` protein, Sso7-like protein

<400> SEQUENCE: 14

Met Val Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Gln Met Leu Glu Lys Ser Gly Lys Lys
    50                  55                  60

<210> SEQ ID NO 15
<211> LENGTH: 6
<212> TYPE: PRT
<213> ORGANISM: Artificial Sequence
<220> FEATURE:
<223> OTHER INFORMATION: synthetic 6-His epitope tag

<400> SEQUENCE: 15

His His His His His His
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic anti-DYKDDDDK epitope tag

<400> SEQUENCE: 16

Asp Tyr Lys Asp Asp Asp Asp Lys
1               5

<210> SEQ ID NO 17
<211> LENGTH: 775
<212> TYPE: PRT
<213> ORGANISM: Artificial Sequence
<220> FEATURE:
<223> OTHER INFORMATION: synthetic consensus DNA polymerase sequence
<220> FEATURE:
<221> NAME/KEY: VARIANT
<222> LOCATION: (25)...(25)
<223> OTHER INFORMATION: Xaa = Lys or Glu
<220> FEATURE:
<221> NAME/KEY: VARIANT
<222> LOCATION: (49)...(49)
<223> OTHER INFORMATION: Xaa = Asp or Glu
<220> FEATURE:
<221> NAME/KEY: VARIANT
<222> LOCATION: (52)...(52)
<223> OTHER INFORMATION: Xaa = Arg or Lys
<220> FEATURE:
<221> NAME/KEY: VARIANT
<222> LOCATION: (56)...(56)
<223> OTHER INFORMATION: Xaa = Gly or Ala
<220> FEATURE:
<221> NAME/KEY: VARIANT
<222> LOCATION: (81)...(81)
<223> OTHER INFORMATION: Xaa = Glu or Thr
<220> FEATURE:
<221> NAME/KEY: VARIANT
<222> LOCATION: (84)...(84)
<223> OTHER INFORMATION: Xaa = Lys or Arg
<220> FEATURE:
<221> NAME/KEY: VARIANT
<222> LOCATION: (87)...(87)
<223> OTHER INFORMATION: Xaa = Leu or Phe
<220> FEATURE:
<221> NAME/KEY: VARIANT
<222> LOCATION: (95)...(95)

```
<223> OTHER INFORMATION: Xaa = Ala or Thr
<220> FEATURE:
<221> NAME/KEY: VARIANT
<222> LOCATION: (98)...(98)
<223> OTHER INFORMATION: Xaa = Asp or Glu
<220> FEATURE:
<221> NAME/KEY: VARIANT
<222> LOCATION: (100)...(100)
<223> OTHER INFORMATION: Xaa = Val or Ile
<220> FEATURE:
<221> NAME/KEY: VARIANT
<222> LOCATION: (104)...(104)
<223> OTHER INFORMATION: Xaa = Pro or Ser
<220> FEATURE:
<221> NAME/KEY: VARIANT
<222> LOCATION: (132)...(132)
<223> OTHER INFORMATION: Xaa = Glu or Asp
<220> FEATURE:
<221> NAME/KEY: VARIANT
<222> LOCATION: (137)...(137)
<223> OTHER INFORMATION: Xaa = Ile or Leu
<220> FEATURE:
<221> NAME/KEY: VARIANT
<222> LOCATION: (166)...(166)
<223> OTHER INFORMATION: Xaa = Asn or Glu
<220> FEATURE:
<221> NAME/KEY: VARIANT
<222> LOCATION: (175)...(175)
<223> OTHER INFORMATION: Xaa = Asn or Lys
<220> FEATURE:
<221> NAME/KEY: VARIANT
<222> LOCATION: (196)...(196)
<223> OTHER INFORMATION: Xaa = Arg or Lys
<220> FEATURE:
<221> NAME/KEY: VARIANT
<222> LOCATION: (197)...(197)
<223> OTHER INFORMATION: Xaa = Val or Ile
<220> FEATURE:
<221> NAME/KEY: VARIANT
<222> LOCATION: (205)...(205)
<223> OTHER INFORMATION: Xaa = Val or Ile
<220> FEATURE:
<221> NAME/KEY: VARIANT
<222> LOCATION: (216)...(216)
<223> OTHER INFORMATION: Xaa = Phe or Leu
<220> FEATURE:
<221> NAME/KEY: VARIANT
<222> LOCATION: (220)...(220)
<223> OTHER INFORMATION: Xaa = Val or Ala
<220> FEATURE:
<221> NAME/KEY: VARIANT
<222> LOCATION: (244)...(244)
<223> OTHER INFORMATION: Xaa = Leu or Ile
<220> FEATURE:
<221> NAME/KEY: VARIANT
<222> LOCATION: (252)...(252)
<223> OTHER INFORMATION: Xaa = Ile or Val
<220> FEATURE:
<221> NAME/KEY: VARIANT
<222> LOCATION: (297)...(297)
<223> OTHER INFORMATION: Xaa = Glu or Lys
<220> FEATURE:
<221> NAME/KEY: VARIANT
<222> LOCATION: (301)...(301)
<223> OTHER INFORMATION: Xaa = Ser or Thr
<220> FEATURE:
<221> NAME/KEY: VARIANT
<222> LOCATION: (318)...(318)
<223> OTHER INFORMATION: Xaa = Val or Ala
<220> FEATURE:
<221> NAME/KEY: VARIANT
<222> LOCATION: (327)...(327)
<223> OTHER INFORMATION: Xaa = Leu or Phe
<220> FEATURE:
<221> NAME/KEY: VARIANT
<222> LOCATION: (331)...(331)
<223> OTHER INFORMATION: Xaa = Ile or Ala
<220> FEATURE:
<221> NAME/KEY: VARIANT
<222> LOCATION: (367)...(367)
```

-continued

```
<223> OTHER INFORMATION: Xaa = Val or Leu
<220> FEATURE:
<221> NAME/KEY: VARIANT
<222> LOCATION: (373)...(373)
<223> OTHER INFORMATION: Xaa = Ser or Asp
<220> FEATURE:
<221> NAME/KEY: VARIANT
<222> LOCATION: (375)...(375)
<223> OTHER INFORMATION: Xaa = Glu or Arg
<220> FEATURE:
<221> NAME/KEY: VARIANT
<222> LOCATION: (389)...(389)
<223> OTHER INFORMATION: Xaa = Tyr or Phe
<220> FEATURE:
<221> NAME/KEY: VARIANT
<222> LOCATION: (408)...(408)
<223> OTHER INFORMATION: Xaa = Ser or Thr
<220> FEATURE:
<221> NAME/KEY: VARIANT
<222> LOCATION: (431)...(431)
<223> OTHER INFORMATION: Xaa = Glu or Asn
<220> FEATURE:
<221> NAME/KEY: VARIANT
<222> LOCATION: (434)...(434)
<223> OTHER INFORMATION: Xaa = Ile or Val
<220> FEATURE:
<221> NAME/KEY: VARIANT
<222> LOCATION: (456)...(456)
<223> OTHER INFORMATION: Xaa = His or Arg
<220> FEATURE:
<221> NAME/KEY: VARIANT
<222> LOCATION: (459)...(459)
<223> OTHER INFORMATION: Xaa = Glu or Asp
<220> FEATURE:
<221> NAME/KEY: VARIANT
<222> LOCATION: (470)...(470)
<223> OTHER INFORMATION: Xaa = Glu or Ala
<220> FEATURE:
<221> NAME/KEY: VARIANT
<222> LOCATION: (478)...(478)
<223> OTHER INFORMATION: Xaa = Lys or Ile
<220> FEATURE:
<221> NAME/KEY: VARIANT
<222> LOCATION: (494)...(494)
<223> OTHER INFORMATION: Xaa = Phe or Tyr
<220> FEATURE:
<221> NAME/KEY: VARIANT
<222> LOCATION: (520)...(520)
<223> OTHER INFORMATION: Xaa = Lys or Glu
<220> FEATURE:
<221> NAME/KEY: VARIANT
<222> LOCATION: (553)...(553)
<223> OTHER INFORMATION: Xaa = Glu or Lys
<220> FEATURE:
<221> NAME/KEY: VARIANT
<222> LOCATION: (554)...(554)
<223> OTHER INFORMATION: Xaa = Pro or Ser
<220> FEATURE:
<221> NAME/KEY: VARIANT
<222> LOCATION: (566)...(566)
<223> OTHER INFORMATION: Xaa = Lys or Asp
<220> FEATURE:
<221> NAME/KEY: VARIANT
<222> LOCATION: (570)...(570)
<223> OTHER INFORMATION: Xaa = Ser or Ala
<220> FEATURE:
<221> NAME/KEY: VARIANT
<222> LOCATION: (585)...(585)
<223> OTHER INFORMATION: Xaa = Val or Lys
<220> FEATURE:
<221> NAME/KEY: VARIANT
<222> LOCATION: (594)...(594)
<223> OTHER INFORMATION: Xaa = Arg or Lys
<220> FEATURE:
<221> NAME/KEY: VARIANT
<222> LOCATION: (597)...(597)
<223> OTHER INFORMATION: Xaa = Val or Leu
<220> FEATURE:
<221> NAME/KEY: VARIANT
<222> LOCATION: (604)...(604)
```

-continued

```
<223> OTHER INFORMATION: Xaa = Val or Ile
<220> FEATURE:
<221> NAME/KEY: VARIANT
<222> LOCATION: (630)...(630)
<223> OTHER INFORMATION: Xaa = Thr or Ala
<220> FEATURE:
<221> NAME/KEY: VARIANT
<222> LOCATION: (642)...(642)
<223> OTHER INFORMATION: Xaa = Lys or Arg
<220> FEATURE:
<221> NAME/KEY: VARIANT
<222> LOCATION: (652)...(652)
<223> OTHER INFORMATION: Xaa = Ala or Ser
<220> FEATURE:
<221> NAME/KEY: VARIANT
<222> LOCATION: (653)...(653)
<223> OTHER INFORMATION: Xaa = Asn or Lys
<220> FEATURE:
<221> NAME/KEY: VARIANT
<222> LOCATION: (686)...(686)
<223> OTHER INFORMATION: Xaa = Lys or Arg
<220> FEATURE:
<221> NAME/KEY: VARIANT
<222> LOCATION: (690)...(690)
<223> OTHER INFORMATION: Xaa = Arg or Lys
<220> FEATURE:
<221> NAME/KEY: VARIANT
<222> LOCATION: (713)...(713)
<223> OTHER INFORMATION: Xaa = Lys or Asn
<220> FEATURE:
<221> NAME/KEY: VARIANT
<222> LOCATION: (721)...(721)
<223> OTHER INFORMATION: Xaa = Phe or Tyr
<220> FEATURE:
<221> NAME/KEY: VARIANT
<222> LOCATION: (764)...(764)
<223> OTHER INFORMATION: Xaa = Val or Thr

<400> SEQUENCE: 17

Met Ile Leu Asp Ala Asp Tyr Ile Thr Glu Glu Gly Lys Pro Val Ile
 1               5                  10                  15

Arg Leu Phe Lys Lys Glu Asn Gly Xaa Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Xaa Glu Val Xaa Lys Ile Thr Xaa Glu Arg His Gly Lys Ile Val Arg
50                  55                  60

Ile Val Asp Ala Glu Lys Val Glu Lys Lys Phe Leu Gly Arg Pro Ile
65                  70                  75                  80

Xaa Val Trp Xaa Leu Tyr Xaa Glu His Pro Gln Asp Val Pro Xaa Ile
                85                  90                  95

Arg Xaa Lys Xaa Arg Glu His Xaa Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Xaa Glu Glu Leu Lys Xaa Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Xaa Glu Ala Lys Val Ile Thr Trp Lys Xaa Ile
                165                 170                 175

Asp Leu Pro Tyr Val Glu Val Ser Ser Arg Glu Met Ile Lys
            180                 185                 190

Arg Phe Leu Xaa Xaa Ile Arg Glu Lys Asp Pro Asp Xaa Ile Ile Thr
        195                 200                 205

Tyr Asn Gly Asp Ser Phe Asp Xaa Pro Tyr Leu Xaa Lys Arg Ala Glu
```

```
                210                 215                 220
Lys Leu Gly Ile Lys Leu Thr Ile Gly Arg Asp Gly Ser Glu Pro Lys
225                 230                 235                 240

Met Gln Arg Xaa Gly Asp Met Thr Ala Val Glu Xaa Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Xaa Ala Trp Glu Xaa Gly Glu Gly
290                 295                 300

Leu Glu Arg Val Ala Lys Tyr Ser Met Glu Asp Ala Lys Xaa Thr Tyr
305                 310                 315                 320

Glu Leu Gly Lys Glu Phe Xaa Pro Met Glu Xaa Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Xaa Ala
                355                 360                 365

Pro Asn Lys Pro Xaa Glu Xaa Glu Tyr Glu Arg Arg Leu Arg Glu Ser
370                 375                 380

Tyr Ala Gly Gly Xaa Val Lys Glu Pro Glu Lys Gly Leu Trp Glu Asn
385                 390                 395                 400

Ile Val Ser Leu Asp Phe Arg Xaa Leu Tyr Pro Ser Ile Ile Ile Thr
                405                 410                 415

His Asn Val Ser Pro Asp Thr Leu Asn Arg Glu Gly Cys Arg Xaa Tyr
                420                 425                 430

Asp Xaa Ala Pro Glu Val Gly His Lys Phe Cys Lys Asp Phe Pro Gly
                435                 440                 445

Phe Ile Pro Ser Leu Leu Lys Xaa Leu Leu Xaa Glu Arg Gln Lys Ile
                450                 455                 460

Lys Thr Lys Met Lys Xaa Ser Gln Asp Pro Ile Glu Lys Xaa Met Leu
465                 470                 475                 480

Asp Tyr Arg Gln Arg Ala Ile Lys Ile Leu Ala Asn Ser Xaa Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Xaa Tyr Ile Glu Phe Val Trp Lys Glu
                515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Xaa Xaa Glu Glu Ile Lys Lys Lys
545                 550                 555                 560

Ala Leu Glu Phe Val Xaa Tyr Ile Asn Xaa Lys Leu Pro Gly Leu Leu
                565                 570                 575

Glu Leu Glu Tyr Glu Gly Phe Tyr Xaa Arg Gly Phe Phe Val Thr Lys
                580                 585                 590

Lys Xaa Tyr Ala Xaa Ile Asp Glu Glu Gly Lys Xaa Ile Thr Arg Gly
                595                 600                 605

Leu Glu Ile Val Arg Arg Asp Trp Ser Glu Ile Ala Lys Glu Thr Gln
                610                 615                 620

Ala Arg Val Leu Glu Xaa Ile Leu Lys His Gly Asn Val Glu Glu Ala
625                 630                 635                 640
```

-continued

```
Val Xaa Ile Val Lys Glu Val Thr Gln Lys Leu Xaa Xaa Tyr Glu Ile
        645             650                 655

Pro Pro Glu Lys Leu Ala Ile Tyr Glu Gln Ile Thr Arg Pro Leu His
            660             665             670

Glu Tyr Lys Ala Ile Gly Pro His Val Ala Val Ala Lys Xaa Leu Ala
            675             680             685

Ala Xaa Gly Val Lys Ile Lys Pro Gly Met Val Ile Gly Tyr Ile Val
        690             695             700

Leu Arg Gly Asp Gly Pro Ile Ser Xaa Arg Ala Ile Leu Ala Glu Glu
705             710             715                 720

Xaa Asp Pro Arg Lys His Lys Tyr Asp Ala Glu Tyr Tyr Ile Glu Asn
            725             730                 735

Gln Val Leu Pro Ala Val Leu Arg Ile Leu Glu Gly Phe Gly Tyr Arg
            740             745             750

Lys Glu Asp Leu Arg Trp Gln Lys Thr Lys Gln Xaa Gly Leu Thr Ser
        755             760             765

Trp Leu Asn Ile Lys Lys Ser
770             775
```